United States Patent [19]
McDermott et al.

[11] Patent Number: 5,597,380
[45] Date of Patent: Jan. 28, 1997

[54] SPECTRAL MAXIMA SOUND PROCESSOR

[75] Inventors: Hugh J. McDermott, Carlton; Andrew E. Vandali, Oak Park, both of Australia

[73] Assignee: Cochlear Ltd., Lane Cove, Australia

[21] Appl. No.: 239,757

[22] Filed: May 9, 1994

Related U.S. Application Data

[63] Continuation-in-part of Ser. No. 92,263, Jul. 14, 1993, abandoned, which is a continuation-in-part of Ser. No. 788,591, Nov. 6, 1991, abandoned.

[30] Foreign Application Priority Data

Jul. 2, 1991 [JP] Japan ................................ 3-161802

[51] Int. Cl.$^6$ ........................................ A01N 1/36
[52] U.S. Cl. ................................. 607/57; 607/137
[58] Field of Search .................. 607/55–57, 115, 607/116, 137; 600/25; 381/68.2, 94; 623/10

[56] References Cited

U.S. PATENT DOCUMENTS

| | | |
|---|---|---|
| 4,207,441 | 6/1980 | Ricard et al. . |
| 4,289,935 | 9/1981 | Zollner et al. . |
| 4,390,756 | 6/1983 | Hoffmann et al. . |
| 4,441,202 | 4/1984 | Tong et al. . |
| 4,515,158 | 5/1985 | Patrick et al. . |
| 4,532,930 | 8/1985 | Crosby et al. . |
| 4,611,598 | 9/1986 | Hortmann . |
| 4,813,417 | 3/1989 | Soli et al. ................................. 607/56 |
| 5,095,904 | 3/1992 | Seligman et al. . |

OTHER PUBLICATIONS

Wilson et al. – "Comparative Studies of Speech Processing Strategies For Cochlear Implants", 90th Annual Meeting of American Laryngological, Rhinological and Otological Society, Inc., Denver, Colorado, Apr. 28, 1987.

*Primary Examiner*—William E. Kamm
*Assistant Examiner*—Jeffrey R. Jastrzab
*Attorney, Agent, or Firm*—Gottlieb, Rackman & Reisman

[57] ABSTRACT

An improved sound processor, with particular application to stimulation of implanted electrode arrays, such as cochlear implants. The processor channelizes received sound signals into at least ten analysis channels to produce amplitude signals for each channel. A predefined number of channels with the largest amplitude are used to modulate stimuli for the implanted array. The predefined number is at least four, and less than or equal to half the number of analysis channels.

8 Claims, 3 Drawing Sheets

SPECTRAL MAXIMA SOUND PROCESSOR

RELATED APPLICATIONS

This is a continuation-in-part to application Ser. No. 092,263 filed Jul. 14, 1993, now abandoned, which was a continuation in part to application Ser. No. 788,591 filed Nov. 6, 1991, now abandoned.

FIELD OF INVENTION

The present invention relates to a method of processing received acoustic data, particularly but not exclusively for stimulating via implanted electrode arrays.

BACKGROUND

The general technique of stimulating via implanted electrode arrays is known from various disclosures, such as U.S. Pat. No. 4,532,930 to Crosby et al; U.S. Pat. No. 4,207,441 to Ricard et al; and U.S. Pat. No. 4,611,598 to Hortmann et al. Such techniques generally involve implanting an electrode array into the cochlea to produce a sensation of hearing, connecting the array by direct or indirect means to a stimulation device, and modulating the stimulations in accordance with a signal. This signal is generally produced by processing in some fashion the electrical output of a microphone.

Many known processing techniques concentrate on utilising models of how the sensation of sound is detected by the brain in response to particular stimuli. Thus, the data is processed to some extent with the object of emphasising particular sorts of information in the stimulation of the electrode array.

In a paper by Wilson et al., Processing Strategies for Cochlear Implants, published in 1988, a processing strategy is disclosed utilising a bank of 4 or 6 bandpass filters, the largest 2 or 4 amplitudes in the defined channels being used as the basis for stimulation. The paper states that using more channels, and selecting more channels from the larger set of channels, will improve performance of the processing strategy. There is no discussion of a preferred number of channels, or of how to choose an appropriate number of channels to select, in the case of more than 6 channels being provided by the filter bank.

SUMMARY OF INVENTION

According to the present invention, electrical signals corresponding to received sound signals are processed by filter mean to provide a signal corresponding to amplitude in at least 10 analysis channels. A predetermined number of the amplitude signals are then chosen as the basis for stimulation, based on those analysis channels having the greatest amplitude, providing the amplitude in the channel exceeds a predefined level. The predetermined number of channels chosen to modulate stimuli is at least 4, and less than or equal to half the number of analysis channels.

Preferably, the array is stimulated at a constant rate and the stimuli are delivered non-simultaneously.

The prior art technique utilising only 6 analysis channels does not, it is believed, provide sufficient information to enable optimal sound discrimination by the user. Using fewer analysis channels generally results in poorer discrimination between similar sound signals. However, it has been determined by the inventors that there is also an upper limit on the number of channels which should be used as the basis for stimulation. The ability to usefully discriminate sounds is likely to decline also if too many channels are used. The resulting extensive spread of stimulation within the cochlea may diminish the user's ability to discriminate frequency information. Selecting fewer channels produces more localised stimulation, from which users can extract information more easily. For example, if all 10 from 10 channels are used as a basis for stimulation, too much information i relation to each sample, with too little discrimination, is presented to a user.

Stimuli are preferably presented sequentially, and presenting each stimulus takes a finite time, thus the time taken for presenting stimuli corresponding to a given sound sample increases as the number of channels selected (and hence the maximum number of stimuli presented per sample period) increases. Consequently, the number of channels selected according to the present sound processing technique operates to place an upper limit on the rate of stimulation. Higher rates of stimulation are more effective at providing users with information about rapidly changing or brief events in the sound signal. Accordingly, the present invention provides an upper limit on the number of channels selected, so as to provide a balance between the quantity and resolution of information in the frequency domain, and resolution in the time domain.

BRIEF DESCRIPTION OF DRAWINGS

The invention will be described with reference to the accompanying figures, in which.

DETAILED DESCRIPTION

Figure 1:
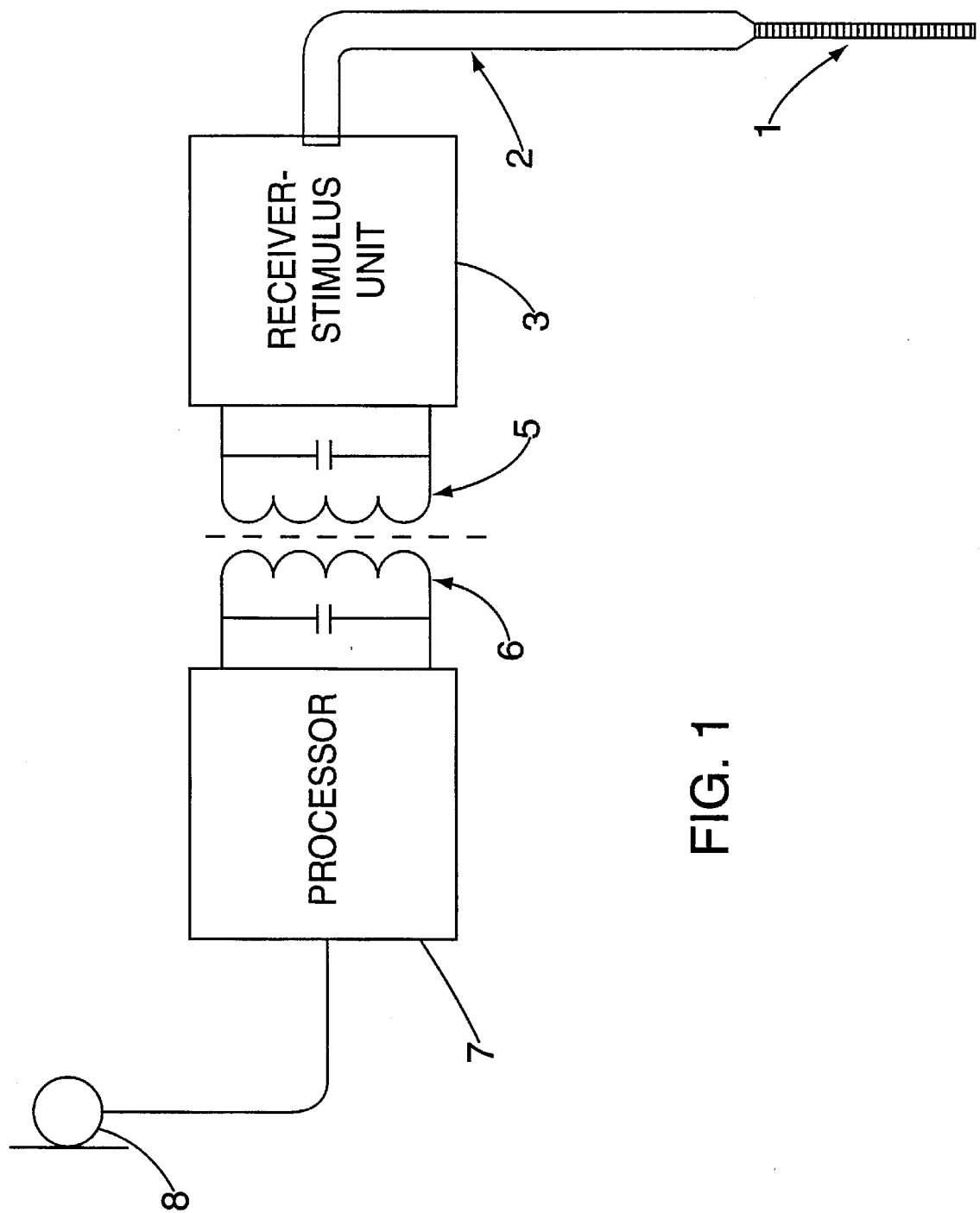
FIG. 1 is a block diagram of an illustrative implanted neural stimulation system.

Referring to FIG. 1, this illustrates an overview of a system for stimulating an electrode array in accordance with a processed signal.

An electrode array 1, implanted into a cochlea, connects via cable 2 to a receiver—stimulator unit (RSU) 3. The entire implanted system may be of conventional type, such as the "Cochlear Mini-System 22".

The implanted system receives control signals and power from an external speech processor unit, preferably via a tuned coil RF system 5, 6 as illustrated. However, any alternative connection technique such as percutaneous connection may be employed.

The coil 6 carries a signal modulated by the processor 7 so as to cause the RSU 3 to stimulate the electrodes in the electrode array in the desired sequence, timing and amplitude.

The processor 7 in turn receives electrical analog signals from a microphone 8 worn by the user.

The present invention is concerned with the operation of the processor and particularly the method of processing the incoming electrical signal.

It is emphasised that while the invention is described in relation to a cochlear implant system, it is also applicable to speech processing in general, hearing aids, voice recognition, speech synthesis and tactile presentation of sound.

Figure 2:
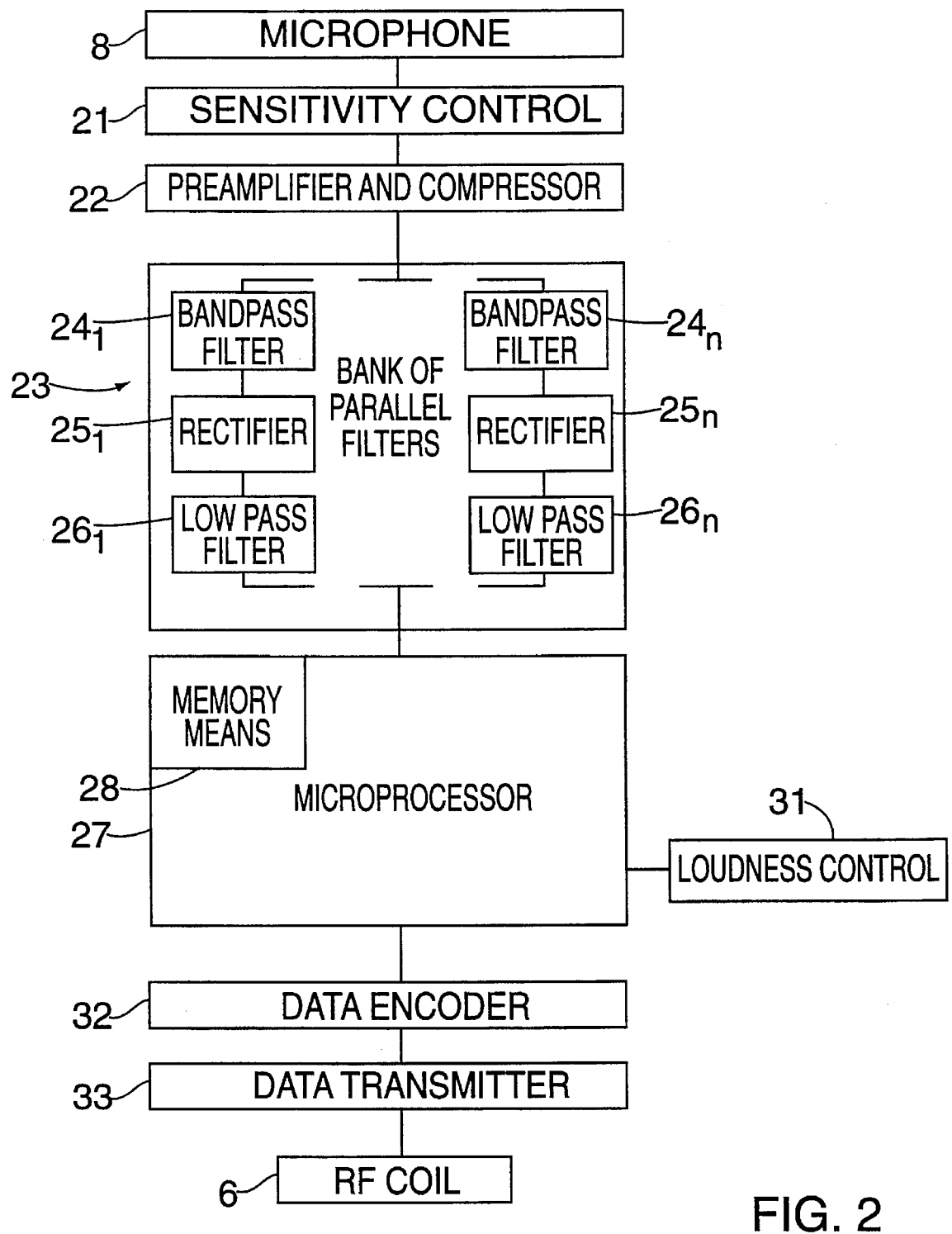
FIG. 2 is a block diagram of a sound processing system according to the present invention.

Referring to FIG. 2, sound received by the microphone 8 produces a corresponding electrical signal. Sensitivity control 21 provides an adjustable attenuation to allow to some extent for the level of ambient sound. The signal is then pre-amplified and optionally compressed at 22.

The signal is then processed by a bank 23 of parallel filters tuned to adjacent frequency channels. In a preferred embodiment there are 16 channels with centre frequencies from 250 to 5400 Hz, and the filter bank is a single chip device. Preferably, filter spacing is linear up to 1650 Hz and logarithmic beyond in the case of an analog implementation.

Each channel in the illustrated analog implementation includes a bandpass filter $24_n$, then a rectifier $25_n$ and low pass filter $26_n$ to provide an estimate of amplitude for each channel. Preferably each low pass filter has a cut-off frequency of about 200 Hz. The output signals from each channel are then digitised.

The digitised outputs are modified by the microprocessor 27 so as to reflect the normal variation of hearing sensitivity with frequency. The set of outputs is multiplied by a set of corresponding coefficients so as to result in a slight increase in system sensitivity at around 400 Hz, a reduction at higher frequencies, and subsequently a gradual increase to a broad peak in sensitivity at about 4 kHz.

The microprocessor than selects the six largest channel amplitudes at intervals of approximately 4 ms. It is noted that this would not normally represent six different spectral peaks, as adjacent channels may share energy from a single spectral peak. It will be appreciated that depending upon the corresponding sound signals, there may be fewer than six or no channels stimulated in a given period, if there is no sound, or sound which is very narrow spectrally.

The selected amplitudes are then converted into stimulus current level. As with known devices, the current levels corresponding to audible threshold and maximum comfortable level for each configuration of electrode stimulation in a particular patient are empirically determined and stored in a memory means 28. The amplitudes are then mapped into the individual stimulus range for each implanted electrode set. An alternative method of converting amplitudes into stimulus levels is to vary pulse widths instead of or as well as current levels. The processor selects the appropriate active electrode for each stimulus pulse according to the frequency of the channel. The data is then encoded at 32, and transmitted at 33 by RF coil 6.

Amplitude mapping refers to the conversion of amplitudes estimated from incoming acoustic signals into levels of electrical stimulation. The electrical dynamic range of each electrode may be defined as the range from threshold to maximum comfortable loudness. The shape of the conversion function is approximately logarithmic; that is, the electrical level is proportional to the log (approximately) of the acoustic signal amplitude obtained from the relevant filter.

Figure 3:
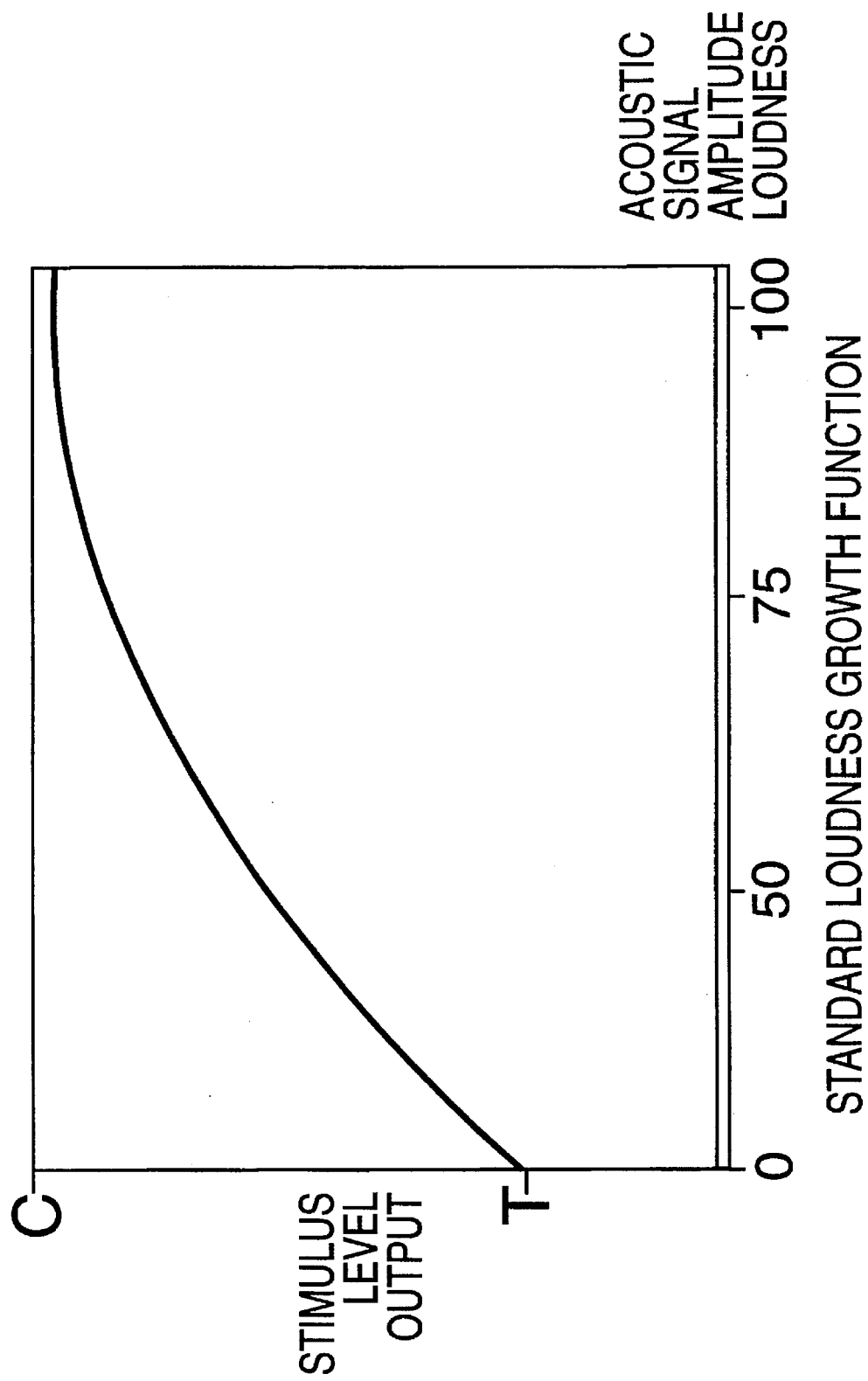
FIG. 3 illustrates graphically the amplitude mapping within the dynamic range of an electrode.

FIG. 3 shows schematically the growth function and the mapping exercise. For each implanted patient, there is a threshold stimulus T for each electrode, and a maximum comfortable level C. The amplitude signal, with a notional value of, say, 0 to 100, is mapped along the growth function curve so as to determine the appropriate stimulus level.

This procedure is well known in the art, and is in the preferred embodiment very similar to that used in the MSP processor manufactured by Cochlear Pty Ltd, and which has been widely used commercially. This technique has been described in, for example, U.S. Pat. No. 5,095,904 to Seligman et al.

Microprocessor 27 is also connected to a loudness control 31, which users find convenient to use in association with the sensitivity control 21. Loudness control 31 essentially allows the current amplitude levels (and/or pulse widths) to be adjusted within a predefined range without affecting system sensitivity to the input signals.

Generally, the 16 most-apical stimulating electrode positions are allocated in tonotopic order to the 16 channels of the filter bank. The channel selection technique ensures that the maximum rate of stimulation on any electrode is 250 Hz.

The term "tonotopic" refers to the relationship between the spatial place of stimulation in the cochlea and the pitch of the hearing sensation perceived, in general, the pitch increases for more-basal locations of stimulation. Accordingly, filter channels of progressively higher frequencies are allocated to active electrodes at progressively more-basal locations in the cochlea. The term "tonotopic" appears in the aforesaid Seligman et al patent, which describes this term in greater detail.

It is emphasised that the six from sixteen channel system described is merely one arrangement and systems with less or more channels of filtering and with less or more channels selected are encompassed within the invention. Other rates of stimulation and alternative temporal ordering of the stimulus pulses may also provide satisfactory or improved performance.

As an alternative, the invention may be implemented using a digital signal processing (DSP) implementation. Preferably this uses a DSP56001 Integrated circuit from Motorola.

One digital Implementation employs a 128-point radix-2 fast fourier transform (FFT) to provide 65 discrete spectral values linearly spaced from 0 to 5.85 KHz (sampling rate= 11.7 KHz). The FFT is computed every 4 ms from a 10.9 ms long time series of speech waveform samples. Each successive FFT computation therefore overlaps the previous and subsequent series by 6.9 ms.

Prior to computation of the FFT the time series is windowed by a shaping function to provide the desired spectral and temporal performance for the filter bank. The windowing function consists of a modified Daniell window (flat top with tapered sides in the frequency domain) modified by a Kaiser window (with theta=pi). It provides at 180 Hz filter bandwidth at −3 dB points. Note the FFT spectral sample spacing is 91 Hz, thus every 2nd sample is omitted leaving 32 spectral samples spaced 182 Hz apart. The DC (0 Hz) value is also omitted.

The 32 discrete spectral samples are then reduced to 16 spectral estimates by summation of power in adjacent spectral samples. The resulting 16-channel filter bank is arranged such that the lowest 8 channels have equal bandwidth and are linearly spaced. The highest 6 channels are preferably arranged for an approximately logarithmic increase in filter bandwidth and spacing. It will be appreciated by those skilled in the art that an exactly logarithmic spacing of channel centre frequencies is not possible in practice in a system utilising FFT in the implementation described. As the available frequencies according to the present embodiment are quantised in units of 91 Hz, it is necessary to compromise the spacings so as to provide approximate logarithmic spacings within the quantisation restrictions of the system. Preferred centre frequencies of the 16 filter channels are:

274, 457, 640, 823, 1005, 1188, 1371, 1554, 1828, 2194, 2559, 2925, 3382, 3747, 4296, 5118 Hz.

Each of the 16 spectral channels is assigned to a unique stimulating electrode position in a tonotopic arrangement. Six electrodes are stimulated during each analysis period (i.e. every 4 ms). The six electrodes that are stimulated are selected based on the instantaneous amplitudes of the 16 spectral components. The six largest spectral components in each analysis period are selected, as in the analog version. The amplitudes of the six selected spectral components are transformed using a loudness growth power function and are then mapped into the dynamic range of the stimulating electrodes. The six stimuli are ordered from largest to smallest amplitudes and are presented to the implantee in quick succession every 4 ms. It will be appreciated that alternative temporal ordering, for example tonotopic ordering, may be used.

The term "loudness power growth function" describes the shape of the conversion function used in amplitude mapping, the principles of which are well known. An example is shown in FIG. 3. This shape is derived from the established results of psycophysical experiments which have shown that the relationship between perceived loudness and the electrical level of the causative stimulation can be approximately by power function. Thus loudness (on a log scale) is directly proportional to the log of the amplitude (the log of a power function is a linear function). In practice, the exact shape of the conversion function can be varied, within limits, to produce better processor performance. The term "loudness power growth function" appears in the aforesaid Seligman et al patent, which describes this term in greater detail.

It is also noted that the present invention results in a relatively constant rate of stimulation, contrary to many prior techniques, however experimental evidence suggests that the perception of sound by users using the inventive speech processor is at least as good as or better than the perception of sound using other processors.

It is further noted that as no assumptions about received sound being speech are made, the system should provide improved performance over known techniques for non-speech sounds.

SELECTION OF ASSOCIATED COMPONENTS AND CIRCUIT DESIGN

In order to obtain satisfactory results with the invention, attention needs to be paid to the following points.

Microphone characteristics and frequency response will affect the quality of signal input to the processor, and some variation of the equalisation technique described above may improve performance.

Attention should also be paid to RF interference between the microphone and the transmitter coil when these are mounted on a common headset. This coupling produces components in the audio range. Signal to noise ratio may be improved by including a suitable preamplifier (e.g. gain 40 dB) at the headset or microphone end of the cable.

It is also necessary to ensure that power supply is properly regulated to avoid ripple and noise.

It will be appreciated that other implementations and variations are possible within the spirit and scope of the invention.

What is claimed is:

1. A sound processing device for an auditory prosthesis, comprising:

means for receiving an electrical signal representing a sound signal having a amplitude;

filter means for providing amplitude signals corresponding to said amplitude in each of a number of spaced frequency analysis channels, said number of analysis channels being at least 10;

means for selecting up to a pre-determined number of the amplitude signals according to the ones of said amplitude signals having the greatest magnitude, said amplitude signals being selected only if the amplitude in the respective analysis channel exceeds a predetermined level, said predetermined number being at least 4, but less than or equal to half the number of analysis channels;

and means for producing a plurality of output signals, each output signal corresponding to one of said selected amplitude signals and hence to one of said frequency channels.

2. A device according to claim 1, wherein said frequency channels are linearly spaced up to about 1650 Hz and approximately logarithmically spaced thereafter.

3. A device according to claim 1, wherein said number of channels is 16, and said predetermined number is 6.

4. A sound processing device for producing stimulus signals for an electrode array of an auditory prosthesis, comprising:

means for receiving an electrical signal representing a sound signal;

filter means for providing amplitude signals corresponding to the amplitude of said sound signal in at least 10 spaced frequency channels;

means for selecting up to a predetermined number of the amplitude signals according to the ones of said amplitude signals having the greatest magnitude, said predetermined number being at least 4, but less than or equal to half the number of channels;

memory for mapping said selected amplitude signals into stored current response characteristics and generating for each signal a corresponding current signal; and means for communicating said corresponding current signals to an electrode array such that electrodes in a location corresponding to a frequency channel are stimulated with the corresponding current signal.

5. A device according to claim 4, further comprising normalizing means for modifying said amplitude signals prior to said means for selecting, such that the amplitude signals are multiplied by a set of coefficients corresponding to a frequency variation of hearing sensitivity based on normal hearing.

6. A device according to claim 4 wherein said number of channels is 16, and said predetermined number is 6.

7. A device according to claim 4, wherein said means for communicating communicates said corresponding current signals as a plurality of sets of stimuli ordered temporally from a largest to a smallest amplitude.

8. A sound processing device for an auditory prosthesis, comprising in combination:

means for receiving an electrical signal representing a sound signal having an amplitude;

filter means for providing amplitude signals corresponding to said amplitude in each of a number of spaced frequency analysis channels, said number of analysis channels being at least 10;

means for selecting up to a predetermined number of the amplitude signals according to the ones of said amplitude signals having the greatest magnitude, said amplitude signals being selected only if the amplitude in the respective analysis channel exceeds a predetermined threshold level, said predetermined number being at least 4, but less than or equal to half the number of analysis channels;

means for producing a plurality of output signals, each output signal corresponding to one of said selected amplitude signals and hence to one of said frequency channels;

and a plurality of electrodes for exciting an auditory nerve, wherein said producing means applies said output signals sequentially at a predetermined rate, each output signal being applied to a corresponding electrode.

\* \* \* \* \*